United States Patent [19]

Prather et al.

[11] Patent Number: 5,335,067
[45] Date of Patent: Aug. 2, 1994

[54] SPECTROPHOTOMETRIC PROBE

[75] Inventors: William S. Prather, Augusta; Patrick E. O'Rourke, Martinez, both of Ga.

[73] Assignee: The United States of America as represented by the United States Department of Energy, Washington, D.C.

[21] Appl. No.: 953,042

[22] Filed: Sep. 29, 1992

[51] Int. Cl.⁵ .............. G01N 21/05; G01N 21/59
[52] U.S. Cl. .................... 356/436; 356/440
[58] Field of Search ........... 356/436, 440, 442, 409, 356/410, 411, 246

[56] References Cited

U.S. PATENT DOCUMENTS

| | | | |
|---|---|---|---|
| 3,204,449 | 7/1965 | Fordyce | 356/439 |
| 3,560,099 | 2/1971 | Boe et al. | 356/246 |
| 3,740,155 | 6/1973 | Keller et al. | 356/246 |
| 3,746,864 | 7/1973 | Tick et al. | 356/436 |
| 3,819,278 | 6/1974 | Muller | 356/442 |
| 3,849,002 | 11/1974 | Hach | 356/103 |
| 4,514,257 | 4/1985 | Karlsson et al. | 356/411 |
| 4,561,779 | 12/1985 | Nagamune et al. | 356/440 |
| 4,725,148 | 2/1988 | Endo et al. | 356/442 |
| 4,740,709 | 4/1988 | Leighton et al. | 250/573 |
| 4,872,356 | 10/1989 | Barnett et al. | 73/866.5 |
| 5,046,854 | 9/1991 | Weller et al. | 356/246 |

FOREIGN PATENT DOCUMENTS

| | | | |
|---|---|---|---|
| 2131191 | 12/1971 | Fed. Rep. of Germany | 356/442 |
| 159140 | 12/1980 | Japan | 356/442 |

Primary Examiner—Richard A. Rosenberger
Attorney, Agent, or Firm—Brian R. Tumm; Harold M. Dixon; William R. Moser

[57] ABSTRACT

A support structure bearing at least one probe for making spectrophotometric measurements of a fluid using a source of light and a spectrophotometer. The probe includes a housing with two optical fibers and a plano-convex lens. A sleeve bearing a mirror surrounds the housing. The lens is separated from the mirror by a fixed distance, defining an interior space for receiving a volume of the fluid sample. A plurality of throughholes extending through the sleeve communicate between the sample volume and the exterior of the probe, all but one hole bearing a screen. A protective jacket surrounds the probe. A hollow conduit bearing a tube is formed in the wall of the probe for venting any air in the interior space when fluid enters. The probe is held at an acute angle so the optic fibers carrying the light to and from the probe are not bent severely on emergence from the probe.

20 Claims, 2 Drawing Sheets

SPECTROPHOTOMETRIC PROBE

The United States Government has rights in this invention pursuant to Contract No. DE-AC09-898R18035 between the U.S. Department of Energy and Westinghouse Savannah River Company.

BACKGROUND OF THE INVENTION

1. Field of the Invention

The present invention relates to spectrophotometry. In particular, the present invention relates to in situ spectrophotometric measurements of fluids.

2. Discussion of Background

It is often necessary to make in situ measurements of fluids in wells, boreholes, storage and process tanks, and so forth. Applications include monitoring groundwater flow, studying the migration of subsurface contaminants, evaluating the progress of clean-up operations at toxic waste sites, detection of toxic or explosive substances, and monitoring the contents of industrial storage tanks.

Many different devices are available for making such measurements, responding to the chemical, electrical, or optical effects of some substance in the fluid. Optical devices with colorimetric and fluorescent indicators can measure parameters such as pH, oxygen or carbon dioxide concentration, the presence and concentration of metal ions, and the presence of organic contaminants such as PCBs. Some optical devices depend on an indicator which exhibits a change in an optical property, such as fluorescence emission, color, and so forth, in response to the fluid. The indicator may be in the form of a coating on an optical fiber. Light is directed through the fluid into the fiber, and changes in light absorption that result from the changed optical properties of the coating are detected.

A substance can often be identified simply by the frequency distribution of the light it absorbs, since the amount of light absorbed at different frequencies depends on the concentration of each component. A typical system for obtaining absorption spectra includes a light source, a sample cell which contains the fluid of interest, and a detector. Light from the source passes through the sample cell, then is focused onto the detector which measures the absorption spectrum of the light. Absorption spectra can be measured for solids, gases, or substances in solution. Measurements taken from a reference sample, such as distilled water, are compared to measurements taken from the fluid sample to help determine the concentrations of various components in the fluid sample.

Where measurements must be made at many different locations, a number of individual devices, or probes, may be connected to a single remotely-located measuring instrument. Measurements are then made by switching between each probe in turn. For monitoring purposes, the probes may be left in place for extended periods of time.

It is well known that retained air in a probe used for optical measurements of a fluid can lead to inaccurate measurements. Thus, irregular reflections from bubbles in the sample cell can affect the light transmission or scattering properties of the fluid. Arrangements for reducing colorimetry or turbidity measurement errors due to air or gas bubbles typically depend on vents and baffles to release bubbles separated from the measurement area of the fluid sample. For example, see Boe, et al. (U.S. Pat. No. 3,560,099), Muller (U.S. Pat. No. 3,819,278), Hach (U.S. Pat. No. 3,849,002), Leighton, et al. (U.S. Pat. No. 4,740,709).

In many applications, there is a need for measurements not only at a number of different locations, but at a range of subsurface depths at each location. For example, when monitoring groundwater transport at a given location, it is desirable to measure fluid flow at several depths. At present, this can only be accomplished by positioning a probe at each desired depth, at each location. The probes are often left in situ for long-term monitoring, which necessitates placing a number of probes at each location. A 100' (about 30.5 m) borehole may be only 3" (about 0.08 m) in diameter. A probe used therein must not only be compact, but must communicate reliably with a remote measuring instrument. Accurate positioning of a probe within such a long, narrow cavity is difficult; accurate deployment of many probes within the same cavity is even more difficult. There is no known apparatus which allows the efficient and accurate placement of a plurality of probes at predetermined positions in a single location.

SUMMARY OF THE INVENTION

According to its major aspects and broadly stated, the present invention is a support bearing at least one probe for making spectrophotometric measurements of a fluid with a source of light and a measuring device such as a spectrophotometer. One end of the probe is held in the support and the other end extends from the support. The probe includes a housing with a planoconvex lens, a fiber terminator, and two optical fibers, one for receiving light from the light source and one for transmitting reflected light from the probe. A sleeve bearing a mirror is slidably mounted on the housing for reflecting the light through an interior space within the probe. The lens is separated from the mirror by a fixed but adjustable distance, defining a sample volume for receiving the fluid. A plurality of holes extends through the sleeve, all but one hole beating a screen.

A jacket is mounted on the probe. A plurality of holes extends through the wall of the jacket, substantially abutting the interior space. A hollow conduit beating a vent tube is formed in the wall of the jacket. The probe is mounted to the support such that the longitudinal axis of the probe intersects the support at an angle $\phi$.

In use, the apparatus is positioned in a well, borehole, or tank. Fluid enters the interior space through the holes in the sleeve and the jacket. Air or gas contained within the volume is displaced by the incoming fluid and exits the probe through the conduit and vent tube. Light from the source is carried by the first optical fiber to the lens, through the sample volume to the mirror. The light is reflected by the mirror and focused by the lens onto the second optical fiber. The reflected light is carried by the second fiber to the measuring device.

The support may carry as tony spaced-apart probes as are needed to adequately monitor a particular site, spaced at convenient positions along the support. Measurements may be made with good vertical resolution, since the uncertainties inherent in positioning a plurality of probes at different subsurface depths are greatly reduced. The compact configuration of the apparatus eliminates the time-consuming process of individually positioning a number of probes at a single measurement site. The apparatus can readily be used in existing wells and boreholes, or in tanks with narrow access openings. It can be used for continuous or intermittent monitoring, as needed for the particular application. A single detector such as a spectrophotometer can accommodate a plurality of probes carried by a single support. Similarly, a network of such apparatus, each bearing a plurality of probes, can be connected to a single detector.

An important feature of the present invention is the support structure. The support is fashioned of any convenient material, preferably polyvinyl chloride (PVC) or similar stock with a diameter of about 1" (2.54 cm ). Alternatively, the support is made of hollow tubing having any convenient inside and outside diameters, or of hollow tubing with solid plugs inserted at intervals for reinforcing the regions where the probes are mounted to the support.

Another feature of the present invention is the probe. The probe includes a housing, a lens holder bearing a planoconvex lens, and two optical fibers. The first fiber is operatively connected to a source of light; the second is operatively connected to a measuring device. A sleeve bearing a mirror is slidably mounted on the housing. When the sleeve is mounted on the housing, the lens is separated from the mirror by a fixed but adjustable distance, defining a sample volume for receiving the fluid. A plurality of holes extends through the sleeve and abuts the sample volume, all but one hole bearing a screen.

A jacket having an open end and a closed end is mounted on the probe. A plurality of holes extend through the wall of the jacket, substantially abutting the holes in the sleeve and the sample volume. The open end of the jacket has two plane faces which intersect at an angle $\phi$. A hollow conduit bearing a vent tube is formed in the wall of the jacket. The longitudinal axis of the probe intersects the support at an angle $\phi$ when the probe is mounted on the support. Thus, one face of the open end of the jacket abuts the support and the other face meets the support at an angle $180° - \phi$.

Still another feature of the present invention is the screens. The screens allow fluid to flow through the holes of the jacket and sleeve into the interior of the probe, but prevent particulate matter such as soil from entering the sample volume. The screens may be stainless steel mesh, spot welded to the sleeve, or a filter material such as those materials marketed under the trade names TYNEX and GORETEX. The mesh size depends on the anticipated subsurface soil conditions. As will be evident, a finer mesh is needed where the subsurface soil includes fine-grained clay and a coarser mesh where it includes only coarse-grained sand or grit.

A further feature of the present invention is the vent tube. The vent tube is disposed above the sample volume, and allows air or gas to escape from the sample volume as fluid enters therein, preventing bubbles in the sample volume from interfering with the accuracy of the measurement. The tube is of a suitable diameter to facilitate the escape of air or gas from the sample volume, preferably no smaller than about 0.8"(2 ram) in diameter. If desired, the vent tube may be connected to a vacuum pump or other device for withdrawing air or gas from the sample volume.

Another feature of the present invention is the angle between the support and the longitudinal axis of the probe. When the probe is mounted on the support, the longitudinal axis of the probe intersects the support at an angle $\phi$. When the apparatus is in use, for example in a borehole, the optical fibers bend at an angle approximately equal to $\phi$ and are directed substantially vertically from the probe to the surface. The preferred range of angles $\phi$ is determined by the particular dimensions of the support and the probe, and the bending radius of the optical fibers. This angle must be greater than approximately 900° to maintain the vent tube above the sample volume. The greater the angle, the smaller the horizontal distance needed to accommodate the support, the probe, and the optical fibers and the narrower the opening in which the apparatus can be used.

Other features and advantages of the present invention will be apparent to those skilled in the art from a careful reading of the Detailed Description of a Preferred Embodiment presented below and accompanied by the drawings.

DETAILED DESCRIPTION OF A PREFERRED EMBODIMENT

Figure 1:
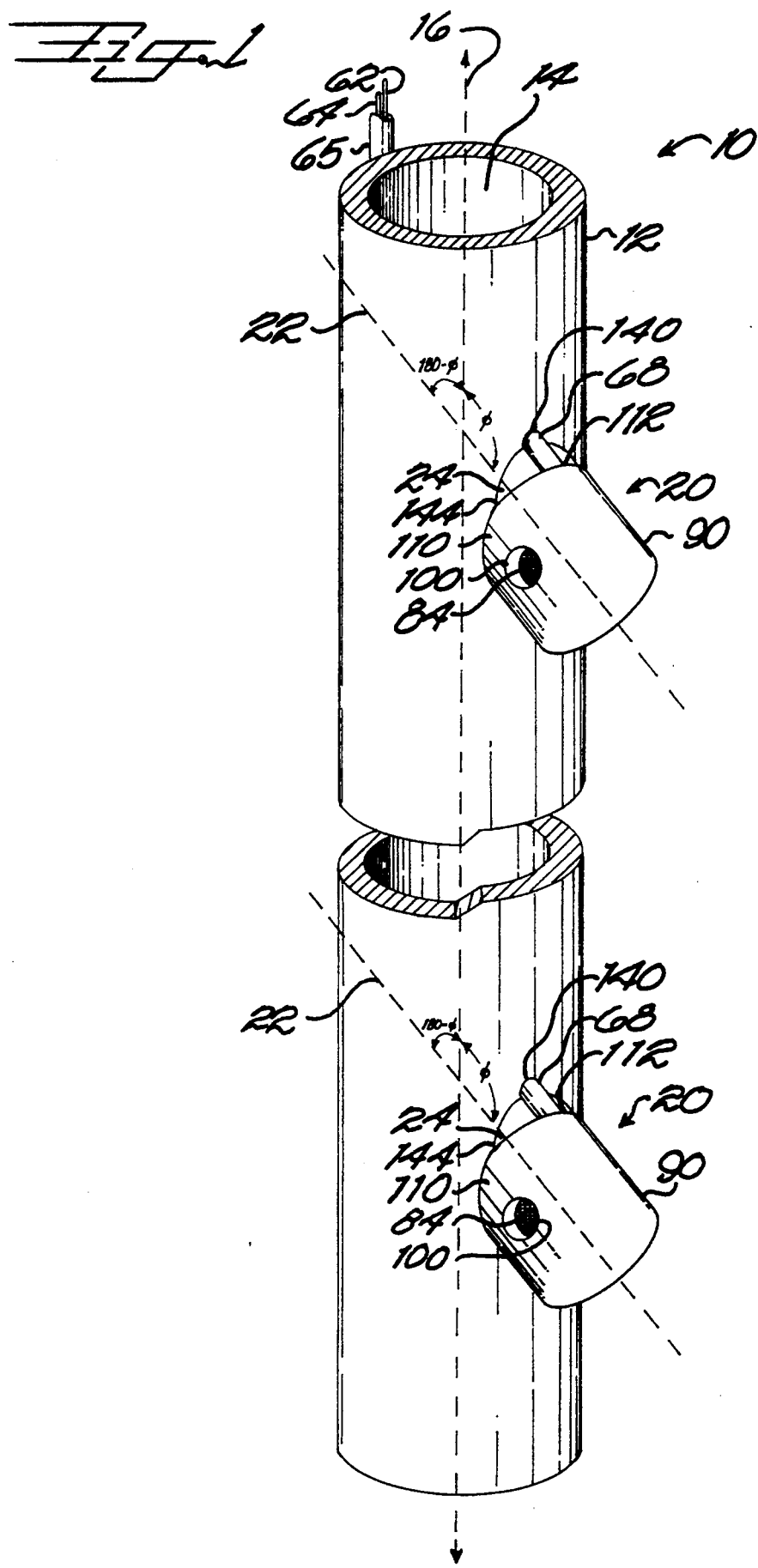
FIG. 1 is a view of an apparatus according to a preferred embodiment of the present invention.

Referring now to FIG. 1, there is shown an apparatus according to a preferred embodiment of the present invention. Apparatus 10 includes support structure 12 having interior 14 and longitudinal axis 16.

Figure 2:
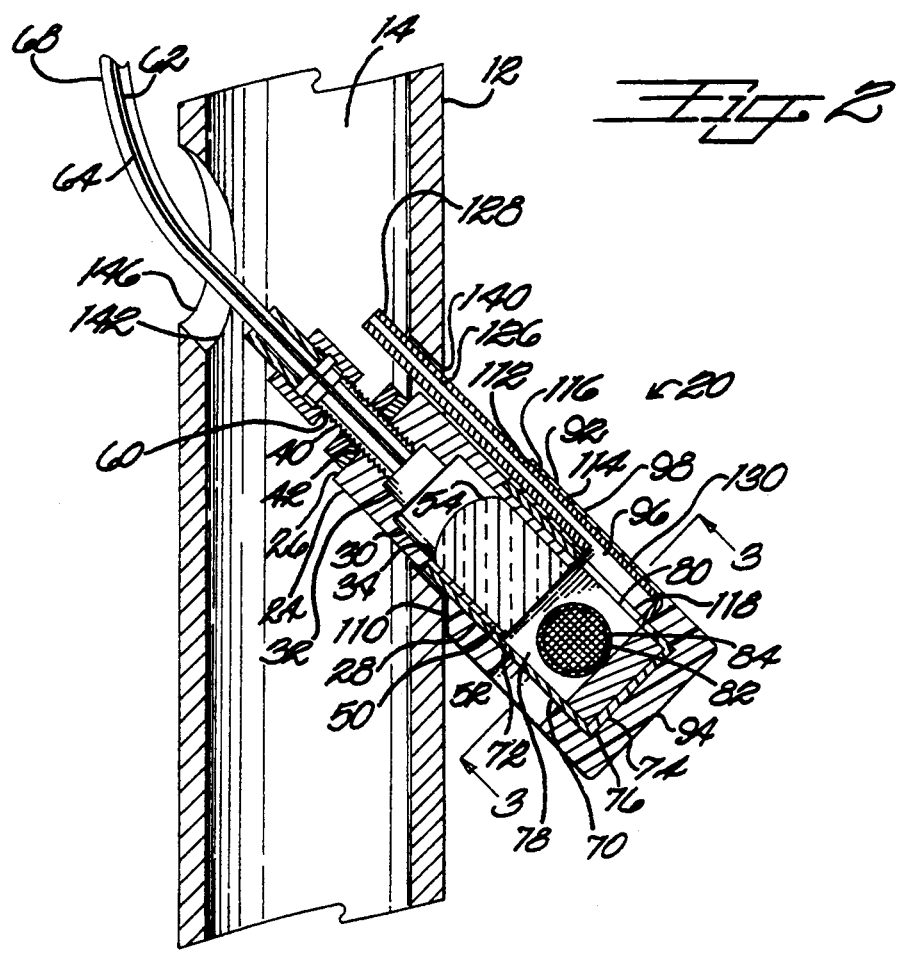
FIG. 2 is a cross-sectional view of a probe according to a preferred embodiment of the present invention.

Support 12 bears at least one optical probe 20 with longitudinal axis 22 (FIG. 2). Probe 20 includes housing 24 having first end 26 and second end 28. Housing 24 bears lens holder 30, with first end 32 and second end 34. Threaded bushing 40 is mounted in hole 42 in first end 26 of housing 24. Fiber terminator 44 is mounted onto bushing 40. Second end 34 of lens holder 28 bears lens 50, having plane face 52 and convex face 54.

Bushing 40 has bore 60 therethrough. Optical fibers 62, 64 extend through bore 60. Bushing 40 is covered by cap 66, and fibers 62, 64 are enclosed by protective casing 68. Fiber 62 carries light from a source of light (not shown) to lens 50; fiber 64 carries light from lens 50 to a measuring instrument such as a spectrophotometer.

Sleeve 70 has first end 72 and second end 74. First end 72 is dimensioned to slidably mount over second end 28 of housing 24. Second end 74 bears minor 76. Thus, the distance between lens 50 and mirror 76 is adjustable by sliding sleeve 70 over second end 28 of housing 24.

Sleeve 70 has a hole 80 and at least one hole 82 therethrough. Preferably, sleeve 70 has two substantially opposing holes 82. Holes 82 are covered by screens 84. As best seen in FIG. 2, when sleeve 70 is mounted over second end 28 of probe housing 24, plane face 52 of lens 50 is separated from mirror 76 by some fixed but adjustable distance, defining sample volume 78. Holes 80, 82 substantially abut sample volume 78.

Figure 3:
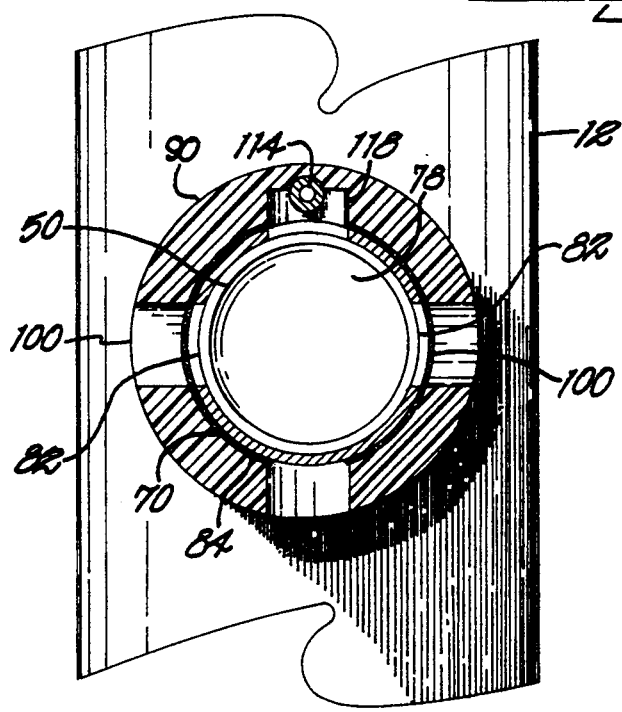
FIG. 3 is a cross-sectional view of a probe according to a preferred embodiment of the present invention through line 3—3 of FIG. 2.

A cross-sectional view of probe 20 is shown in FIG. 3, through line 3—3 of FIG. 2. As shown in FIGS. 2 and 3, jacket 90, having open end 92, closed end 94, interior 96 and wall 98, is slidably mounted on sleeve 70. At least one hole 100 extends through wall 98 into interior 96. Preferably, jacket 90 has two opposing holes 100. Holes 100 may be circular or of any convenient shape. Open end 92 of jacket 90 has two plane faces 110, 112, intersecting at an angle $\phi$. When face 110 is oriented in a substantially vertical direction, face 112 is at an angle of $180° - \phi$ from the vertical, as best seen in FIG. 1.

Hollow conduit 114, having first end 116 and second end 118, is formed in wall 98 of jacket 90. First end 116 extends through face 112; second end 118 abuts sample volume 78. Conduit 114 carries vent tube 126 having first end 128 and second end 130. When jacket 90 is mounted on probe 20, holes 100 substantially abut holes 82 of sleeve 70, and hole 80 of sleeve 70 substantially abuts end 118 of conduit 114, as shown in FIG. 3.

Cavity 140 extends into interior 14 of support 12. Hole 142, having first end 144 and second end 146, extends through support 12. Cavity 140 and hole 142 are shaped and positioned so that cavity 140 receives first end 128 of vent tube 126 when probe 20 is mounted in first end 144 of hole 142. Cavity 140 and hole 142 are substantially aligned with axis 22 of probe 20. As best seen in FIG. 1, axis 16 of support 12 and axis 22 of probe 20 intersect at an angle $180° - \phi$. Thus, face 110 of jacket 90 abuts support 12 and face 112 meets support 12 at an angle $\phi$ when probe 20 is mounted in hole 142. Optical fibers 62, 64 exit support 12 at second end 146. Fibers 62, 64 eventually bend at an angle approximately equal to $\phi$ and extend upwards substantially parallel to support 12.

In use, support 12 bearing at least one probe 20 is positioned in a well, borehole, or tank. In order to permit the escape of air or gas from sample volume 78, apparatus 10 is arranged so that conduit 114 and vent tube 126 are disposed above sample volume 78. While apparatus 10 is illustrated in FIG. 1 in substantially vertical alignment, it will be understood that apparatus 10 may readily be used in any convenient position including horizontal.

Fluid enters sample volume 78 through holes 100 in jacket 90 and holes 82 in sleeve 70. If apparatus 10 is in a well or borehole, screens 84 allow the passage of fluid, but prevent particulate matter such as soil or grit particles from entering sample volume 78. As fluid enters volume 78, any air or gas contained within the volume is displaced by the fluid and exits through hole 80 and conduit 114. Thus, inaccuracies due to such phenomena as irregular reflections from bubbles in sample volume 78 are reduced.

Light from a source (not shown) is carried by optical fiber 62 to lens 50, through sample volume 78 to mirror 76. The light is reflected by mirror 76 and focused by lens 50 onto optical fiber 64. This reflected light is carded by fiber 64 to a conveniently-located measuring device such as a spectrophotometer (not shown).

In a preferred embodiment of the present invention, support 12 is fashioned of substantially cylindrical stock such as polyvinyl chloride (PVC), TEFLON, or similar material. Support 12 has an outside diameter of about 1" (2.54 cm). Cavity 140 and hole 142 are preferably circular in cross section, with the former having a diameter of approximately 0.8" (2 mm) and the latter a diameter of approximately ½" (1.27 cm). Support 12 may, however, be any convenient elongated structure for supporting probes 20. Support 12 may be made of hollow PVC tubing, or PVC tubing with solid plugs inserted at intervals to reinforce the regions carrying probes 20.

Support 12 has any desired number of conveniently-positioned cavities 140 and holes 142 for receiving a plurality of probes 20 and vent tubes 126. If desired, cavities 140 and holes 142 may be located at different radial positions on support 12, so that probes 20 extend outwards from support 12 in different directions. While probes 20 are shown with axes 22 intersecting axis 16 of support 12, probes 20 may be displaced from axis 16. That is, holes 142 may be offset from the center of support 12, or take the form of notches or other convenient structures for supporting probes 20.

Probe 20 is approximately 2-½" (6.35 cm) long and has an outside diameter of about ½" (1.27 cm). Hole 80 and holes 82 are about 5/16" (0.79 cm) in diameter. Probe 20 is friction-fitted into hole 142 of support 12. Probe 20 may, however, be mounted in hole 142 by any convenient means, including cemented or screwed into hole 142. When probe 20 is mounted in hole 142, about 1-½" (3.81 cm) of the length of probe 20 is outside support 12. It will be understood that the particular dimensions of probe 20, and likewise the dimensions of support 12, may be varied without departing from the spirit of the present invention.

Lens holder 30 is any convenient type of lens holder, in which is mounted planoconvex lens 50. Lens holder 30, bushing 40, probe housing 24 and mirror 76 are preferably fabricated of stainless steel, while lens 50 is quartz. However, these and other parts of probe 20 may be fabricated of any convenient materials which are suitable for the expected conditions. Casing 68 is a flexible, protective material such as PVC or other plastic film.

Screens 84 allow fluid to flow through holes 82 of sleeve 70 into the interior of probe 20, but prevent particulate matter from entering sample volume 78. Screens 84 may be stainless steel mesh, spot welded or otherwise attached to sleeve 70. The mesh size depends on the anticipated conditions. A finer mesh is needed where the subsurface soil includes fine-grained clay and a coarser mesh where it includes only coarse-grained sand or grit. Alternatively, screens 84 may be a filter material such as those materials marketed under the trade names TYNEX and GORETEX.

Screens 84 are fitted to holes 82 in sleeve 70. Alternatively, a single screen 84 may surround sample area 78, held in place between sleeve 70 and jacket 90. If this type of screen 84 is preferred, an opening is formed in screen 84 where screen 84 abuts end 118 of conduit 114, since the material of screen 84 may impede the free flow of air or gas into conduit 114.

Jacket 90 is preferably machined from PVC stock, but may be formed of any convenient material including stainless steel. Jacket 90 has an outer diameter of about 1" (2.54 cm) and an inner diameter of about ½" (1.27 cm) dimensioned to receive probe 20. Wall 98 is about ¼" (0.64 mm) thick. Holes 100 are approximately 5/16" (0.79 cm) in diameter. Conduit 114 may conveniently be formed by drilling hole 120 through wall 98 into interior 96 of jacket 90, and using the access thus provided to form cavity 122 in opposing wall 98. Conduit 124 is formed in wall 98 to meet cavity 122, so that the combination of cavity 122 and conduit 124 forms conduit 114.

Vent tube 126 is of sufficient diameter to allow air or gas to escape from sample volume 78 as fluid enters therein, preferably no smaller than about 0.8" (2 mm) in diameter. Vent tube 126 is preferably a corrosion-resistant material such as stainless steel, but may be a material such as PVC, TEFLON, or other plastic tubing if convenient. Vent tube 126 may be configured as shown in FIG. 1, with end 130 carded by cavity 140 of support 12. Alternatively, end 130 may be located outside support 12. If support 12 is hollow, end 130 may be positioned in the interior of support 12.

If desired, vent tube 126 is connected to a syringe, vacuum pump or other device for controlling the flow of air in tube 126. By this means, air or gas may be withdrawn from sample volume 78 to facilitate the entry of fluid therein. After a measurement has been made, the fluid is expelled from sample volume 78 by reversing the flow of air.

When probe 20 is mounted in support 12, axis 22 of probe 20 intersects axis 16 of support 12 at an angle $\phi$. The preferable range of angles $\phi$ is determined by the particular dimensions of support 12 and probe 20, and especially by the bending radius of optical fibers 62, 64. This last depends on the fiber diameter and materials, but is typically about $\frac{3}{4}''$ (1.91 cm). Also, as noted above, conduit 114 and vent tube 126 are disposed above sample volume 78 to allow the escape of air from volume 78.

When apparatus 10 is in use, for example in a vertical borehole, fibers 62, 64 bend at an angle approximately equal to $\phi$ and are directed substantially vertically from probe 20 to the surface. Fibers 62, 64 may be outside support 12 as illustrated in FIG. 1, or carried inside support 12 if support 12 is hollow. The minimum horizontal width needed to accommodate support 12, probe 20 and fibers 62, 64 depends directly on $\phi$. This angle must be 90° or greater to maintain conduit 114 above sample volume 78. A right-angle bend ($\phi = 90°$) in fibers 62, 64 yields a minimum width of approximately 3.25" (8.26 cm) for the combination of fibers 62, 64 and a 2.5"-long (6.35 cm) probe. Larger angles require smaller widths: about 2.3" (5.84 cm) for $\phi = 135°$; about 1.9" (4.83 cm) for $\phi = 150°$. Thus, the larger the angle, the narrower the opening in which apparatus 10 can be used. Preferably, $\phi$ is greater than approximately 135°. Thus probe 20 is held by support 12 at an acute angle measured from downward vertical to the axis of probe 20 in order that optic fibers 62, 64 are bent at as large an obtuse angle with respect to the axis of probe 20 as possible.

As noted above, support 12 carries at least one probe 20. Support 12 may conveniently carry as many spaced-apart probes 20 as are needed to adequately monitor a particular site. Probes may be spaced at any convenient positions along support 12, depending on the particular conditions at the site. For example, a 100' (about 30.5 m) support may have probes at 10' (about 3.05 m) intervals, or 1' (about 0.3 m) or smaller intervals if more detailed data are required. This capability allows for measurements with good vertical resolution, since the uncertainties inherent in positioning a plurality of probes at different subsurface depths in a single well or borehole are greatly reduced. The compact configuration of apparatus 10 also eliminates the time-consuming process of positioning a plurality of probes at a single measurement site. The probes need not be individually positioned at a site but are placed in known, predetermined positions along support 12 before apparatus 10 is deployed at the measurement site.

Apparatus 10, as illustrated in FIGS. 1–3 and described herein, can readily be used in a hole no larger than 3" (about 7.62 cm) in diameter. Thus, apparatus 10 can be used in existing wells and boreholes, or in tanks with narrow access openings. Even where a new borehole is needed, the compact configuration of apparatus 10 ensures that there will be minimal disturbance of pre-existing conditions at the site. Even though drilling a new borehole disturbs the ambient subsurface conditions, equilibrium is reestablished within a relatively short period of time. Apparatus 10 can be used for continuous or intermittent monitoring, as needed for the particular application.

Probe 20, as described above, is an absorbance probe for spectrophotometric measurements. However, probe 20 may be any convenient type of probe for remote optical measurements. Probe 20 may, for example, include colorimetric or fluorescent indicators for measuring the pH or dissolved gas content of the fluid in sample volume 78.

It will be evident that a single detector can readily accommodate a plurality of probes 20 carried by apparatus 10. Similarly, a network of such apparatus 10, each apparatus bearing a plurality of probes 20, can be connected to a single detector. A single spectrophotometer system, or other measuring system, can be used to monitor such a network of apparatus 10 to develop a space-time profile of the area of interest. Such a network could be implemented, for example, to map groundwater transport or monitor the migration of chemicals soils.

The apparatus of the present invention allows for real-time monitoring of fluids in wells, boreholes, and storage tanks. It can be used to study subsurface fluid transport or to monitor a site for the presence of contaminants. For example, an apparatus 10 might be placed near an underground storage tank. Measurements made from time to time would indicate whether or not the tank is leaking.

It will be apparent to those skilled in the art that many changes and substitutions can be made to the preferred embodiment herein described without departing from the spirit and scope of the present invention as defined by the appended claims.

What is claimed is:

1. An apparatus for performing spectrophotometric measurements of a fluid, said apparatus for use with a source of light and a spectrophotometer, said apparatus comprising:

a support having a longitudinal axis; and a probe having a longitudinal axis, a first end and a second end, said first end of said probe carried by said support, said second end extending from said support, said longitudinal axis of said probe being held at an acute angle with respect to said longitudinal axis of said support, said probe in optical communication with said spectrophotometer and said light source, said probe having means formed in said second end for receiving a fluid and means for transmitting light through said fluid in said receiving means from said source of light to said spectrophotometer, means for venting gas present in said receiving means, said venting means in fluid communication with and above said receiving means and oriented so that, when fluid enters said receiving means and said gas separates from said fluid, said gas rises to said venting means, and means for controlling a flow of gas, said controlling means in fluid communication with said venting means so that said controlling means enables said venting means to vent said gas.

2. The apparatus as recited in claim 1, wherein said acute angle is not more than approximately 45°.

3. The apparatus as recited in claim 1, wherein said receiving means further comprises an interior space through which light from said light source is directed, and said second end of said probe has at least one throughhole for communication between the exterior of said probe and said interior space and through which throughhole fluid may enter said interior space.

4. The apparatus as recited in claim 1, wherein said probe further comprises means for preventing particles from entering said receiving means when said fluid enters said receiving means.

5. The apparatus as recited in claim 1, wherein said probe has a protective jacket on said second end.

6. The apparatus as recited in claim 1, wherein said receiving means further comprises an interior space across which light from said light source is transmitted and a throughhole for fluid communication between said interior space and the exterior of said probe and through which throughhole said fluid may enter said interior space, and said transmitting means further comprises:
 a first optical fiber connected to said first end of said probe, said first optical fiber in optical communication with said light source;
 a second optical fiber connected to said first end of said probe, said second optical fiber in optical communication with said spectrophotometer,
 said first and said second optical fibers positioned at an end of said interior space; and
 a mirror carried by said probe and positioned at an opposing end of said interior space so that light from said first optical fiber is reflected by said mirror and received by said second optical fiber.

7. The apparatus as recited in claim 1, wherein said controlling means supplies gas to said receiving means, said controlling means expelling fluid from said receiving means as said gas enters said receiving means.

8. The apparatus as recited in claim 1, wherein said receiving means includes an interior space across which light from said light source is transmitted, wherein said second end of said probe has at least one throughhole for communication between said interior space and the exterior of said probe, and wherein said apparatus further comprises a sleeve slidable on said second end of said probe, said sleeve having at least one throughhole so that fluid may enter said interior space when said throughhole of said sleeve overlaps said throughhole of said second end of said probe, and wherein said transmitting means further comprises:
 a first optical fiber connected to said first end of said probe, said first optical fiber in optical communication with said light source;
 a second optical fiber connected to said first end of said probe, said second optical fiber in optical communication with said spectrophotometer,
 said first and said second optical fibers positioned at an end of said interior space: and
 a mirror carried by said sleeve and positioned so that light from said first optical fiber is reflected by said mirror and received by said second optical fiber.

9. An apparatus for performing spectrophotometric measurements of a fluid, said apparatus for use with a source of light and a spectrophotometer, said apparatus comprising:
 a support having a longitudinal axis; and
 at least two longitudinally spaced-apart probes, each of said probes having a longitudinal axis, a first end and a second end, said first end of said each probe carded by said support, said second end extending from said support, said longitudinal axis of said each probe being held at an acute angle with respect to said longitudinal axis of said support, said each probe in optical communication with said spectrophotometer and said light source,
 said each probe having means formed in said second end for receiving a fluid and means for transmitting light through said fluid in said receiving means from said source of light to said spectrophotometer,
 means for venting gas present in said receiving means, said venting means in fluid communication with and above said receiving means and oriented so that when fluid enters said receiving means and said gas separates from said fluid, said gas rises to said venting means, and
 means for controlling a flow of gas, said controlling means in fluid communication with said venting means so that said controlling means enables said venting means to vent said gas.

10. The apparatus as recited in claim 9, wherein said acute angle is not more than approximately 45°.

11. The apparatus as recited in claim 9, wherein said receiving means further comprises:
 an interior space through which light from said light source is directed, and said second end of said probe has at least one throughhole for communication between the exterior of said probe and said interior space and through which throughhole fluid may enter said interior space; and
 means for preventing particles from entering said interior space when said fluid enters said receiving means.

12. The apparatus as recited in claim 9, wherein said each probe further comprises:
 an interior space through which light from said light source is directed, and said second end of said probe has at least one throughhole for communication between the exterior of said probe and said interior space and through which throughhole fluid may enter said interior space;
 means for preventing particles from entering said interior space when said fluid enters said receiving means; and
 a protective jacket on said second end.

13. The apparatus as recited in claim 9, wherein said receiving means further comprises an interior space across which light from said light source is transmitted and a throughhole for fluid communication between said interior space and the exterior of said probe and through which throughhole said fluid may enter said interior space, and said transmitting means further comprises:
 a first optical fiber connected to said first end of said each probe, said first optical fiber in optical communication with said light source;
 a second optical fiber connected to said first end of said each probe, said second optical fiber in optical communication with said spectrophotometer,
 said second optical fibers positioned at an end of said interior space; and
 a mirror carried by said each probe and positioned at an opposing end of said interior space so that light from said first optical fiber is reflected by said mirror and received by said second optical fiber,
 said first and said second optical fibers emerging from said first end of said each probe and bending at an obtuse angle to follow said support to said spectrophotometer.

14. The apparatus as recited in claim 9, wherein said receiving means of said each probe includes an interior space across which light from said light source is transmitted, said second end of said each probe having at least one throughhole for fluid communication between said interior space and the exterior of said probe, and wherein said each probe further comprises:
 a first optical fiber connected to said first end of said probe, said first optical fiber in optical communication with said light source;
 a second optical fiber connected to said first end of said probe, said first optical fiber in optical communication with said spectrophotometer,
 said first and said second optical fibers positioned at an end of said interior space, said first and said second optical fibers emerging from said first end of said each probe and bending at an obtuse angle to follow said support to said spectrophotometer;
 a sleeve slidable on said second end of said probe, said sleeve having at least one throughhole so that, when said throughhole of said sleeve overlaps said throughhole of said probe, fluid may enter said interior space; and
 a mirror carried by said sleeve and positioned so that light from said first optical fiber is reflected by said mirror and received by said second optical fiber.

15. An apparatus for performing spectrophotometric measurements of a fluid, said apparatus for use with a source of light and a spectrophotometer, said apparatus comprising:
 a support having a longitudinal axis; and
 a plurality of longitudinally spaced-apart probes, each of said probes having a longitudinal axis, a first end and a second end, said first end of said each probe carried by said support, said second end extending from said support, said longitudinal axis of said each probe being held at an angle with respect to said longitudinal axis of said support, said each probe having an interior space defined therein and at least one throughhole for fluid communication between said interior space and the exterior of said probe,
 said each probe in optical communication with said spectrophotometer and said light source,
 said each probe having means for transmitting light through said fluid in said interior space from said source of light to said spectrophotometer.
 means for venting gas present in said receiving means, said venting means in fluid communication with and above said receiving means and oriented so that when fluid enters said receiving means and said gas separates from said fluid, said gas rises to said venting means, and
 means for controlling a flow of gas, said controlling means in fluid communication with said venting means so that said controlling means enables said venting means to vent said gas.

16. The apparatus as recited in claim 15, wherein said transmitting means further comprises:
 a first optical fiber connected to said first end of said each probe, said first optical fiber in optical communication with said light source;
 a second optical fiber connected to said first end of said each probe, said second optical fiber in optical communication with said spectrophotometer,
 said first and said second optical fibers positioned at an end of said interior space; and
 a mirror carried by said each probe and positioned at an opposing end of said interior space so that light from said first optical fiber is reflected by said mirror and received by said second optical fiber,
 said first and said second optical fibers emerging from said first end of said each probe and bending at an obtuse angle to follow said support to said spectrophotometer.

17. The apparatus as recited in claim 15, wherein transmitting means further comprises:
 a first optical fiber connected to said first end of said each probe, said first optical fiber in optical communication with said light source;
 a second optical fiber connected to said first end of said each probe, said second optical fiber in optical communication with said spectrophotometer,
 said first and said second optical fibers positioned at an end of said interior space;
 a mirror carried by said each probe and positioned at an opposing end of said interior space so that light from said first optical fiber is reflected by said mirror and received by said second optical fiber; and
 a lens for directing light across said interior space from said first optical fiber to said mirror and reflected light from said mirror to said second optical fiber,
 said each probe being held by said support at an acute angle,
 said first and said second optical fibers emerging from said first end of said each probe and bending at an obtuse angle to follow said support to said spectrophotometer.

18. The apparatus as recited in claim 17, wherein said obtuse angle is at least 135° and said acute angle is less than 45°.

19. The apparatus as recited in claim 15, wherein said each probe further comprises:
 means for preventing particles from entering said interior space when said fluid enters interior space; and
 a protective jacket on said second end.

20. The apparatus as recited in claim 15, wherein said each probe further comprises:
 a first optical fiber connected to said first end of said probe, said first optical fiber in optical communication with said light source;
 a second optical fiber connected to said first end of said each probe, said second optical fiber in optical communication with said spectrophotometer,
 said first and said second optical fibers positioned at an end of said interior space, said first and said second optical fibers emerging from said first end of said each probe and bending at an obtuse angle to follow said support to said spectrophotometer;
 a sleeve slidable on said second end of said probe, said sleeve having at least one throughhole so that, when said throughhole of said sleeve overlaps said throughhole of said probe, fluid may enter said interior space;
 a mirror carded by said sleeve and positioned at an opposing end of said interior space so that light from said first optical fiber is reflected by said mirror and received by said second optical fiber; and
 a lens for directing light across said interior space from said first optical fiber to said mirror and from said mirror to said second optical fiber.

* * * * *